United States Patent [19]

Nelen

[11] Patent Number: 5,134,278
[45] Date of Patent: Jul. 28, 1992

[54] DEVICE FOR SIMULTANEOUSLY INSPECTING AN OBJECT FOR DEFECTS AND DEBRIS

[75] Inventor: Lucien J. Nelen, Goor, Netherlands

[73] Assignee: 501 Heuft-Qualiplus B.V., Deventer, Netherlands

[21] Appl. No.: 480,643

[22] Filed: Feb. 14, 1990

[30] Foreign Application Priority Data

Feb. 14, 1989 [NL] Netherlands .................. 8900356
May 31, 1989 [NL] Netherlands .................. 8901380

[51] Int. Cl.$^5$ ............................................. G01N 9/04
[52] U.S. Cl. .................................. 250/223 B; 356/240
[58] Field of Search ............... 250/223 R, 223 B, 225, 250/226; 356/239, 240, 364, 369, 241; 209/524, 526

[56] References Cited

U.S. PATENT DOCUMENTS

| | | | |
|---|---|---|---|
| 4,083,637 | 4/1978 | Ellinger et al. | 250/223 B |
| 4,136,930 | 1/1979 | Gomm et al. | 250/223 B |
| 4,180,722 | 12/1979 | Clewans | 250/226 |
| 4,221,961 | 9/1980 | Peyton | 250/223 B |
| 4,520,388 | 5/1985 | Kellie | 358/107 |
| 4,551,627 | 11/1985 | Reich | 250/223 B |
| 4,650,326 | 3/1987 | Nagamine et al. | 356/240 |
| 4,682,023 | 7/1987 | Yoshida | 250/223 B |
| 4,943,713 | 7/1990 | Yoshida | 250/223 B |

FOREIGN PATENT DOCUMENTS

| | | |
|---|---|---|
| 0222959 | 11/1985 | European Pat. Off. . |
| 0263618 | 9/1987 | European Pat. Off. . |
| 3413027 | 6/1984 | Fed. Rep. of Germany . |
| 2024415 | 6/1979 | United Kingdom . |

Primary Examiner—David C. Nelms
Assistant Examiner—S. Allen
Attorney, Agent, or Firm—Willian Brinks Olds Hofer Gilson & Lione

[57] ABSTRACT

A device for inspecting an object for defects and debris having a first light and a second light to create two images of the object, and a system of mirrors and lenses to direct the images to a sensing station, typically a video camera. A first embodiment uses two sources of light, a first parallel annular bundle and a second diffuse source, to inspect an open holder, such as an aluminum can without a lid, for defects and debris. A second embodiment uses two sources of diffuse light to inspect a cylindrical glass tube, such as a fluorescent light bulb, for defects and debris.

21 Claims, 4 Drawing Sheets

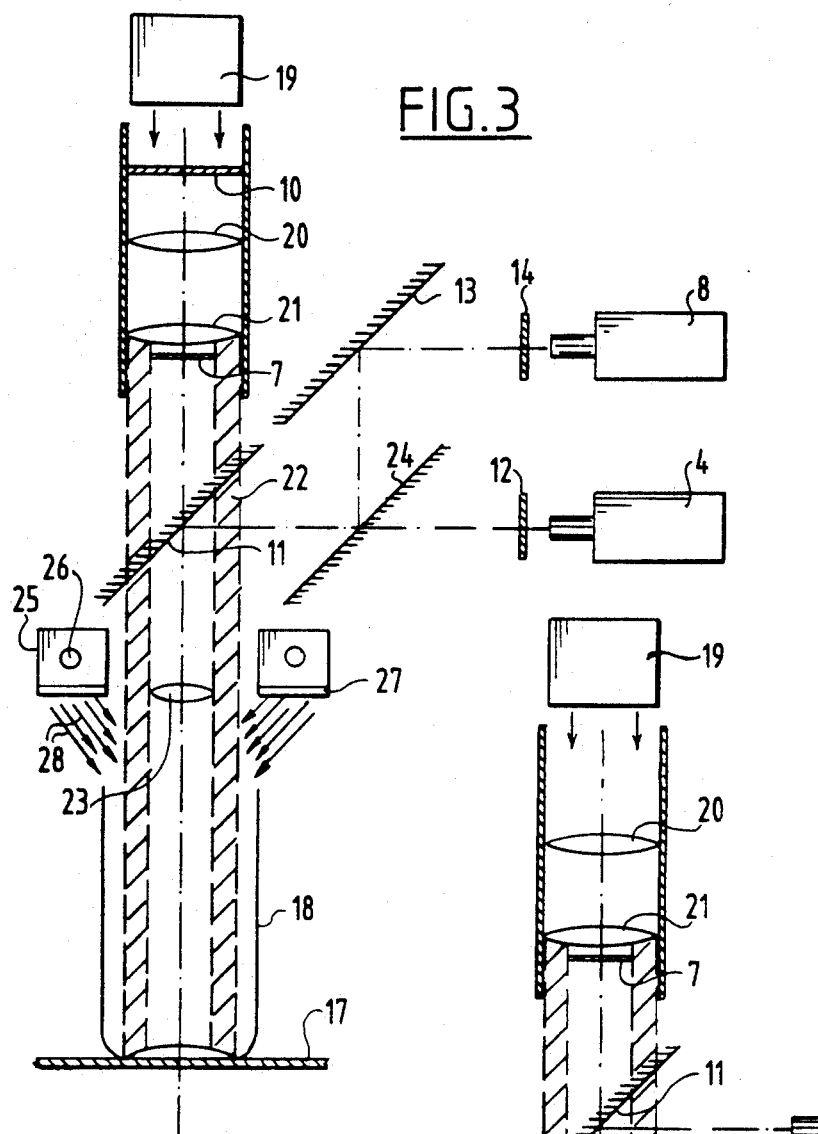
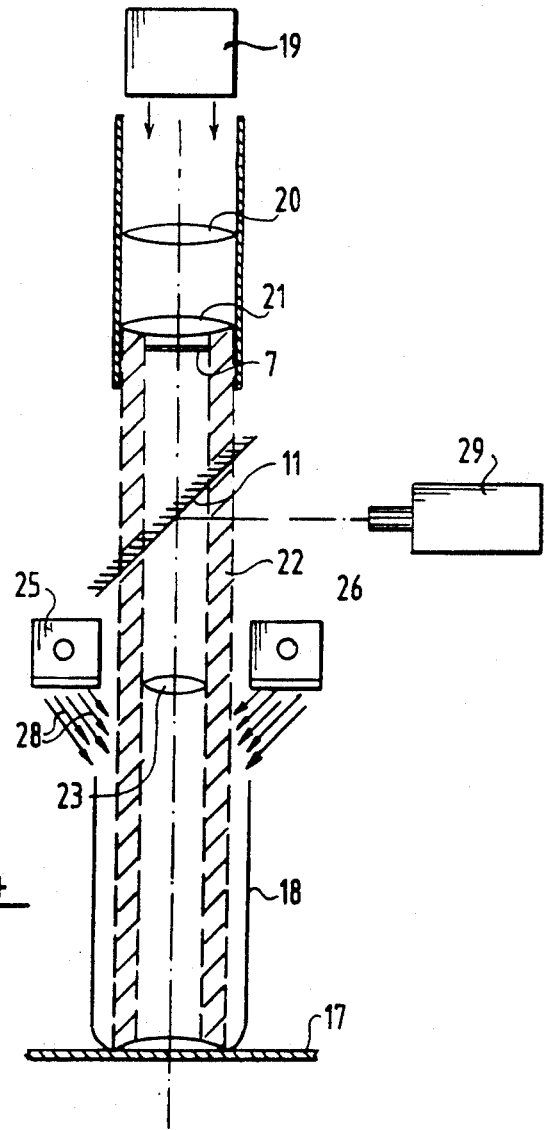

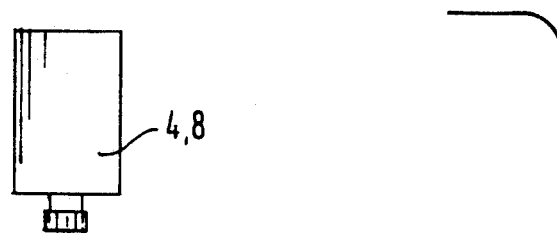
FIG.12
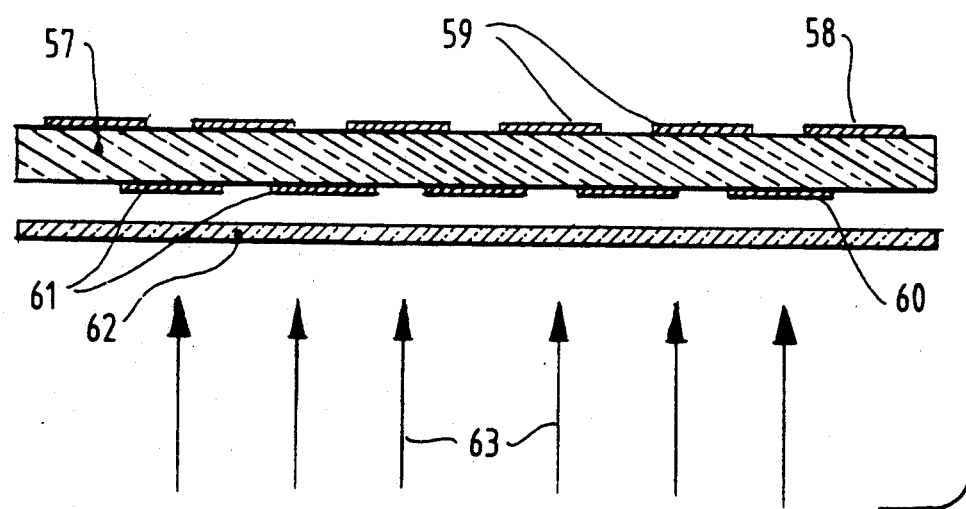

DEVICE FOR SIMULTANEOUSLY INSPECTING AN OBJECT FOR DEFECTS AND DEBRIS

The invention relates to a method for inspecting an object or a series of successively supplied objects for deviations such as form errors, dirt, cracks and so on, comprising the following steps of:

1) providing at least one illuminating station for emitting electromagnetic radiation of a chosen type, 2) providing at least one associated sensing station which is arranged for sensing the electromagnetic radiation emitted by the illuminating station, 3) providing an object for inspection, and 4) arranging in alignment the or each illuminating station, the or each associated sensing station and the object, such that the or each sensing station can form an image of the object illuminated by the associated illuminating station.

Such a method is known. In a known method an object for inspection, for example a glass jar, is transported by means of a conveyor device to a illuminating station and an associated sensing station. The illuminating station can, for example, be arranged to generate a flash at the moment the arrival of the object for inspection is determined. The sensing station, in particular a video camera, senses the image of the object for inspection and feeds that to a central processing unit for instance, which can be coupled with pushing means for pushing out a rejected object. The object subjected in this manner to a first inspection is subsequently carried to a second inspection station with a second illuminating station and a second sensing station, which inspection station differs from the first in order to be able to determine a second type of deviation.

FIG. 1 shows a conveyor device 1 for transporting glass jars 2. A lamp 3 generates a flash at the moment the jar 2 has arrived at the place of inspection. A video camera 4 senses the image of the jar 2 and if necessary transmits to central control means (not drawn) a rejection signal which can serve for controlling push-out means placed downstream of the conveyor device. Light passes through the jar 2 in this manner. This method of illumination is known as bright field illumination. This method is very suitable for sensing, for example, dirt.

The jar 2 is subsequently further transported in the direction of arrow 5 to the position indicated by 2'. Located there is a second inspection station, consisting of a second lamp 6 which generates a flash at the moment the jar 2' has arrived. Because a round, opaque disc 7 is located above the lamp 6 in the middle, light does not pass directly through the jar 2' as described above, but illuminating takes place according to the dark field principle. Under normal conditions a video camera 8 does not therefore sense light but can only ascertain the presence of particular errors of form or cracks, namely deviations which result in transmitting by the jar 2' of light in the direction of the video camera 8.

According to this known art, use has therefore to be made for determining two different types of deviation of two separate inspection stations, each consisting of a illuminating station and an sensing station.

The drawback of the above described known inspection method is that these two separate inspections take up a lot of space and require extra control means.

The invention has for its object to offer a simpler method which is considerably simpler and thereby cost-saving. The invention also has for its object to offer a method providing considerable gains in space.

To this end the method according to the invention is characterized by the following step of:

5) providing only one illuminating station and/or only one sensing station, which illuminating station transmits electromagnetic radiation of at least two types and which sensing station can sense electromagnetic radiation of these at least two types, wherein the image formed from the radiation of the one type can give information about deviations of the first type and the image formed from radiation of the second type can give information about deviations of the second type etc., such that two or more types of deviation can be determined simultaneously.

In a particular embodiment the method can be characterized by the following step of:

6) performing step 5) such that the directions of travel of the electromagnetic radiation of the at least two types differ mutually.

For this purpose the method can for instance be characterized by the following step of:

7) performing step 6) such that one type of radiation is substantially a directed bundle and that another type of radiation is substantially diffuse.

Use can also be made of another embodiment which is characterized by the following step of:

8) performing step 5) such that the polarization directions of the electromagnetic radiation of the at least two types differ mutually.

Another manner of discrimination which also works very well can be achieved with a variant which is characterized by the following step of:

9) performing step 5) such that the spectral compositions of the at least two types of electromagnetic radiation differ.

A known device for performing the known method comprises:

1) at least one illuminating station for emitting electromagnetic radiation of a chosen type;

2) at least one associated sensing station arranged for sensing the electromagnetic radiation emitted by the illuminating station;

3) support means for carrying an object for inspection;

4) wherein the or each illuminating station, the or each associated sensing station and the support means are aligned such that the or each sensing station can form an image of the object illuminated by the associated illuminating station.

Such a device has already been described above with reference to FIG. 1.

The device according to the invention is characterized by only one illuminating station and/or only one sensing station, which illuminating station transmits electromagnetic radiation of at least two types and which sensing station can sense electromagnetic radiation of these at least two types, wherein the image formed from radiation of one type can give information about deviations of a first type and the image formed from radiation of a second type can give information about deviations of a second type etc., such that two or more types of deviation can be determined simultaneously.

A preferred embodiment displays the feature that the one sensing station is arranged for simultaneous, separate sensing of all types of electromagnetic radiation.

For example, for inspecting glass containers the dark field detection method can be markedly improved by illuminating the bottom of the container not only from the outside, as will be discussed hereafter with reference to FIG. 2, but also through the "black" disc. To this end the device then displays the feature that the illuminating station is arranged for emitting through-passing, indirect electromagnetic radiation and comprises for this purpose:

a source for electromagnetic radiation which is placed for through-passing illumination of an object for inspection, and dark field means comprising, from the electromagnetic radiation source, a diffusor, a first pattern of strips opaque to the electromagnetic radiation, for example concentric rings, and a second pattern of strips opaque to the electromagnetic radiation, which two patterns are placed at a distance above one another such that the lines of the one pattern cover the free spaces between the lines of the other pattern.

As a result of this configuration, for instance glass splinters and the like are now not only illuminated from the outside, i.e. from the annular diffuse light-source around the black disc, but also, as it were, through the disc, though not directly but exclusively indirectly, so that when an object is fault-free no electromagnetic radiation reaches the sensing station, and this only occurs in the case of a deviation.

The method and device according to the invention provide the option of performing at least two inspections at one inspection position.

The invention will now be elucidated with reference to the annexed drawing. In the drawing:

FIG. 3 shows an inspection device according to the invention in a second embodiment;

FIG. 4 shows an inspection device according to the invention in a third embodiment;

FIG. 12 shows a cross section through an alternative illuminating station.

Figure 1:
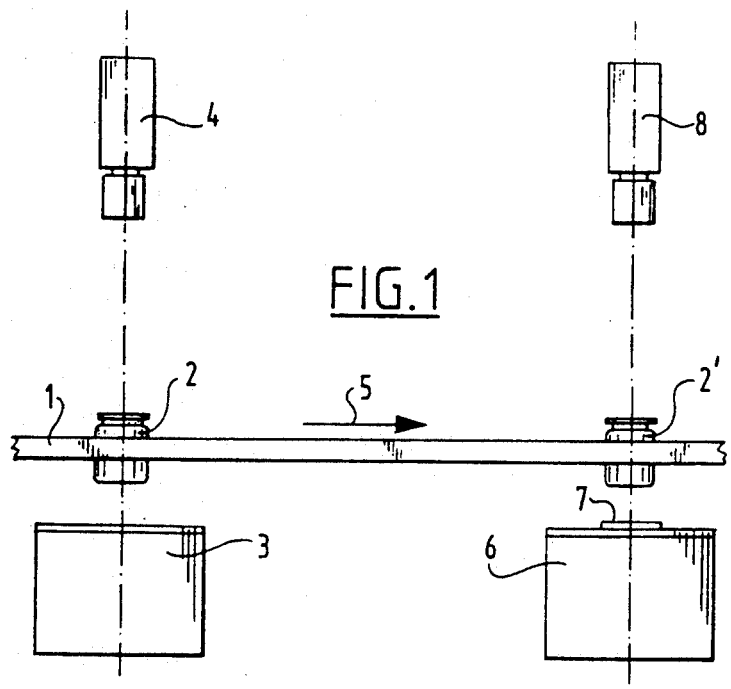
FIG. 1 shows a schematic side view of the inspection device according to the state of the art already discussed above.

For the description of FIG. 1, reference is made to the above.

Figure 2:
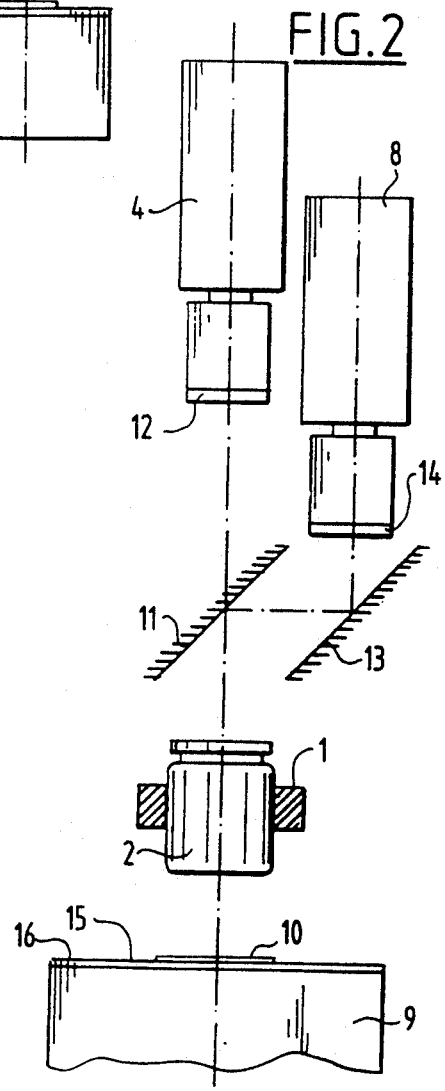
FIG. 2 shows a schematic side view of an inspection device according to the invention in a first embodiment.

FIG. 2 shows the jar 2 which is carried by the conveyor device 1 to above a lamp 9 which is covered in the middle by a filter 10 which allows through all radiation of a wavelength above 600 nm and cuts out all radiation of a smaller wavelength.

The red light allowed through by the filter 10 passes through the jar 2. The radiation allowed through passes through a semi-transparent mirror 11 and enters the video camera 4 via a filter 12. The filter 12 is of the same type as the filter 10 and thus allows through red light. The camera 4 therefore senses an image similar to the camera 4 according to FIG. 1.

The semi-transparent mirror 11 transmits via a mirror 13 another portion of the light to the video camera 8 via a filter 14. The filter 14 is of the type that allows through only radiation of a wavelength smaller than 600 nm. As a result hereof no image of the jar 2 formed by light passing through will be sensed by the camera 8. For this camera 8 the filter 10 therefore functions as the black disc 7 according to FIG. 1.

However, the light-emitting upper surface 15 of the lamp 9 is covered by the filter 10 only in its central portion. The edge zone 16 can emit light in the same way as the lamp 6 with the black disc 7 as in FIG. 1. This light-emitting edge 16 therefore acts to form dark field illumination for the jar 2. Since the radiation emitted via the edge 16 also contains wavelengths which can be allowed through by the filter 14 the camera 8 is hereby capable of sensing a dark field image of the jar 2.

It will be apparent from the above that two inspections for different deviations can now be carried out simultaneously at one inspection location.

FIG. 3 shows a conveyor belt 17 which supplies an open aluminum holder 18 for inspection. A first lamp 19 emits light via the filter 10 to a lens system 20, 21. The outgoing bundle is parallel. Situated in the middle on the exit side of the system 20, 21 is a black disc 7, whereby a cylindrical, parallel bundle 22 is directed into the holder 18 via the semi-transparent mirror 11. This bundle is reflected by the upwardly convex bottom of the holder 18 and directed at a very small angle onto the cylindrical wall of the holder 18 where it is again reflected. A perfectly cylindrical holder without errors of form will emit the light reflected by the cylindrical wall such that this travels beyond the range of an imaging lens 23. Only in the case of, for example, a dent will red light be allowed through by the lens 23 to the semi-transparent mirror 11 where the red light corresponding with the dent reaches the video camera 4 via a semi-transparent mirror 24 via the red filter 12.

Extending around the imaging lens 23 is an annular light source 25. This comprises an annular flash light 26 and a blue diffusor 27. This matt glass diffusor gives off more or less diffuse light to the interior of the can 18, as symbolically indicated with arrows 28. The can 18 is internally illuminated in diffuse blue. The blue image of the can cannot pass through the red filter 12, and only the blue radiation reflected by the mirror 24 can reach the camera 8 via the mirror 13 and the blue filter 14.

FIG. 4 shows a variant wherein the light source corresponds with that according to FIG. 3, but where only one video camera 29 is used. If required, the colour information in the video signal can serve for discriminating between different deviations.

Figure 5:
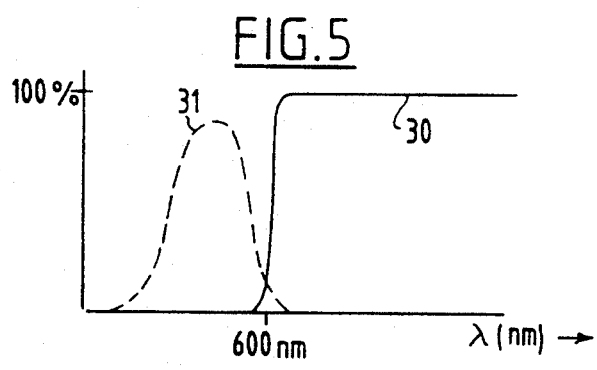
FIG. 5 shows the transmission characteristics of spectral-selective filters for use in the invention.

FIG. 5 shows in an unbroken line the transmission characteristic 30 of the red filters 10, 12 while the transmission characteristic 31 of the diffusor 27 and the blue filter 14 is indicated with a broken line. It will be apparent that in particular the transmission characteristic 30 is especially sharp so that there need be no fear of information cross-talk between both inspection systems. If required use could optionally also be made of illuminating means which emit electromagnetic radiation with a very limited band width, for example sources with a line spectrum wherein one line or a limited wave length field is allowed through. In this context a combination of for instance a mercury lamp and a sodium lamp may be envisaged. It will be otherwise apparent that all sorts of other types of sources can also be considered.

Figure 6:
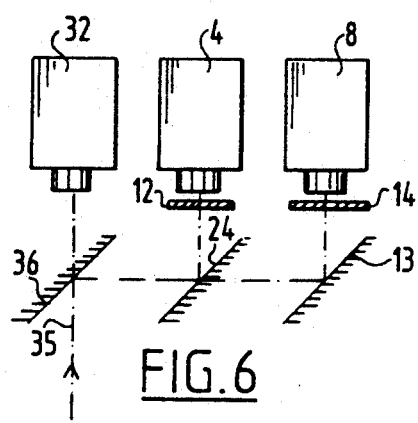
FIG. 6 shows a highly schematic detail of a fourth embodiment.

FIG. 6 shows a detail of a variant wherein use is made of three video cameras 4, 33, 8.

The incident light or other electromagnetic radiation designated with 35 coming from the object for inspection is directed onto a so-called dichroic mirror 36. This allows radiation of the one wavelength field through to the camera 32 and reflects another portion in the direction of semitransparent mirror 24. Reference is made to FIG. 3 for the further optical route.

Figure 7:
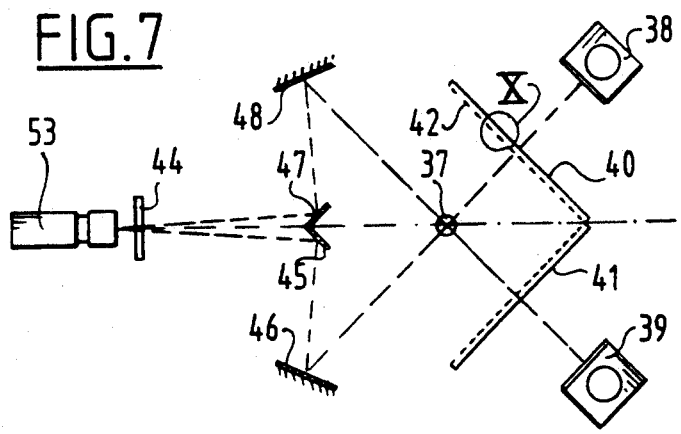
FIG. 7 shows a schematic side view of a fifth embodiment.

FIG. 7 shows a disposition for inspecting a fluorescent lamp 37 or at least the pre-manufactured glass housing thereof.

Use is made of two flash lights 38, 39, which illuminate diffusor plates 40 and 41 respectively. As can be seen more clearly in FIG. 10, these diffusor plates display a red filter formed as a grating 42 of parallel strips 43, for example of the same material as the filter 10 or 12. Via a polarization filter 44 acting against sensing of direct reflections and via respective mirrors 45, 46 and 47, 48 a video camera 53 senses the tube 37 in two directions, respectively illuminated by the lamps 38 and 39.

There are various types of deviations or faults which have to be sensed in the tube, such as air bubbles in the glass, stripes, enclosures, small stones, material deficiencies. For a good inspection it is required that the entire periphery of the tube be inspected. The disposition according to FIG. 7 is arranged to this end.

Attention is drawn to the fact that the tube 37 can pass through the inspection station in an axial direction, for example at a determined speed, whereby all deficiencies along the entire length can be detected.

The inspection according to FIG. 7 takes place on a basis of light refraction. Non-transparent particles are traced by determining a transmission-difference. A disposition of the same type as according to FIG. 2 or an equivalent thereof can also be employed as sensing station.

Figure 8:
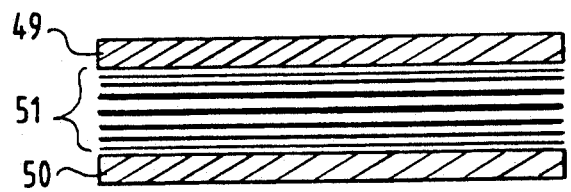
FIG. 8 shows the image of a perfect fluorescent lamp.

FIG. 8 shows a video image consisting of two inspection areas which correspond respectively with the lamp 39 and the lamp 38.

Figure 9:
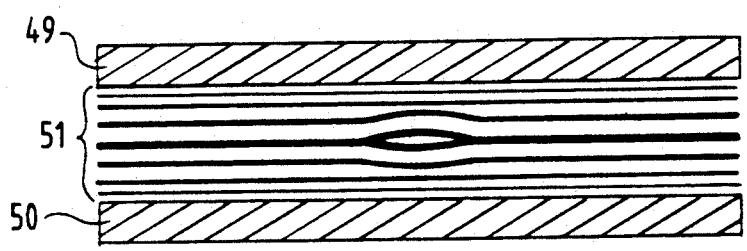
FIG. 9 shows the image of a fluorescent lamp with a deviation in the glass.

FIG. 9 shows as example a disturbance of the image from which is apparent that this is a case of a fault in the glass seen by the camera 53. This senses non-transparent faults in any position, in contrast to the situation wherein the grating-pattern consists of non-transparent strips, and small, non-transparent faults which fall onto a strip are not detected.

The overlap areas 49, 50 are composed of lines which overlap each other after diffraction. The remaining area 51, 51' is the inspection area. It will be apparent that this inspection area must be large enough to sense deviations over the entire periphery of the tube 37 at the two angles.

With regard to FIG. 9 it is further noted the line direction of the video image corresponds with the longitudinal direction of the grating strips 43.

Attention is drawn to the fact that with the inspection according to FIG. 7 the camera 53 is focused on the front surface of the diffusor plates 40, 41. With the methods of inspection discussed heretofore, focusing always takes place on the object 2, 18.

Figures 10, 11:
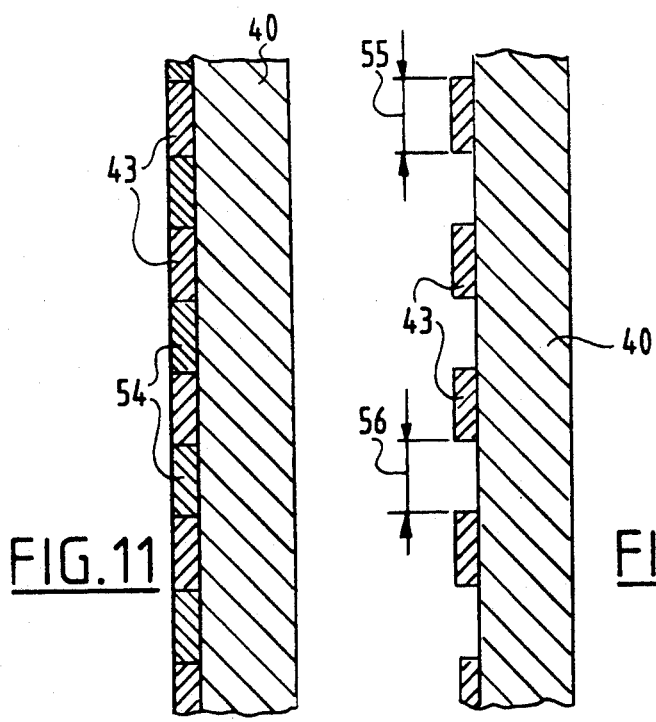
FIG. 10 shows the detail X according to FIG. 7.
FIG. 11 is a view corresponding with FIG. 10 of a preferred embodiment of the diffusor with grating.

In order to ensure that the grey value of the grating strips 43 corresponds with the areas situated therebetween use can be made of the variant drawn in FIG. 11, wherein these intermediate areas are provided with grey filters 54. During sensing of a diffusor plate according to FIG. 11 through a red filter a homogeneous red surface will therefore be sensed.

FIG. 10 shows the breadth 55 and the mutual distance 56 of the grating strips 43. These quantities influence the size of the inspection area on the tube and the dimensions of the minimal detectable deviation. Broadly speaking:

The smaller the breadth and the mutual distance, the greater the overlap area will be, and smaller deviations can be better detected.

The greater the breadth and the mutual distance the smaller the overlap area will be, and smaller deviations will be less well detected.

The more the breadth and the mutual distance deviate from one another, the less well glass deviations will always be detected.

As a result of the invention the detection of nontransparent faults has become independent of the grating pattern.

FIG. 12 finally shows a disposition for dark field illuminating. This arrangement comprises a glass plate 57 which comprises on its upper surface a first pattern 58 of strips, for example concentric rings, opaque to the electromagnetic radiation, and comprises on its underside a second pattern 60 of strips 61 opaque to the electromagnetic radiation, which patterns are placed above one another at a distance the size of the thickness of the glass plate 57 such that the strips of the one pattern 58, 60 cover the free spaces between the strips of the other pattern 60, 58. Under the plate 57 is situated a diffusor 62 under which is placed the radiation source (not drawn). This transmits electromagnetic radiation indicated with arrows 63. This electromagnetic radiation is wholly screened off in the direction of the sensing station 4, 8 (see FIG. 2) by the opaque patterns 58, 60. Only by obliquely through-falling radiation can deviations and faults be illuminated and result in image forming in the sensing station 4, 8. It will be apparent that, for glass bottles for instance, patterns of concentric rings are most suitable. For use in a disposition for checking fluorescent tubes, as explained with reference to FIG. 7-11, patterns of straight strips can be applied.

I claim:

1. A device for detecting defects and debris in an open holder, the holder having an upwardly convex bottom ad cylindrical sides, the device comprising:

a first illuminating station placed to illuminate the inner surface of the upwardly convex bottom of the open holder, the first illuminating station comprising a first light with an outer area an a middle area, a opaque disk covering the middle area, and a lens system positioned so that the first illuminating station illuminates the inner surface of the upwardly convex bottom with a first parallel bundle of light and creates a first image of the upwardly convex bottom;

a second illuminating station placed to illuminate the inner surfaces of the open holder, the second illuminating station comprising a second annular light and a second diffusion plate positioned to cover the second annular light so that the second illuminating station illuminates the inner surfaces of the open holder with a second diffuse light and creates a second image of the inside of the open holder;

a sensing station to sense the first image and the second image;

a mirror station for directing the first image and the second image to the sensing station;

a lens placed within the first parallel bundle of light to direct the first image to the mirror station only when a defect is present in the object.

2. A device for detecting defects and debris in an open holder, the holder having an upwardly convex bottom and cylindrical sides, the device comprising:

a first illuminating station placed to illuminate the inner surface of the upwardly convex bottom of the open holder with a first parallel bundle of light and create a first image of the upwardly convex bottom;

a second illuminating station placed to illuminate the inner surfaces of the open holder with a second diffuse light and create a second image of the inside of the open holder;

a sensing station to sense the first image and the second image for defects in the open holder;

a mirror station for directing the first image an the second image to the sensing station;

an imaging lens placed within the first parallel bundle of light to direct the first image to the mirror station only when a defect is present in the object.

3. The device of claim 2 wherein the first illuminating station comprises a first light with an outer area and a middle area, an opaque disk covering the middle area, and a lens system positioned so that the first illuminating station emits a first parallel bundle of light.

4. The device of claim 2 wherein the second illuminating station comprises a second annular light and a diffusion plate positioned to cover the second annular light so that the second illuminating station emits a second diffuse light.

5. A device for detecting defects and debris in a cylindrical glass housing comprising:

a first illuminating station positioned to illuminate the housing with a first diffuse light and create a first image;

a second illuminating station positioned to illuminate the housing with a second diffuse light and create a second image;

a sensing station to sense the first image and the second image so as to detect defects and debris in the housing;

a first system to direct the first image to the sensing station;

a second system to direct the second image to the sensing station a polarization filter placed so that the sensing station only senses the first image and the second image after they have passed through the polarization filter.

6. The device of claim 5 wherein the first illuminating station comprises a first light having a first diffusion plate so that the first illuminating station emits a first diffuse light.

7. The device of claim 4 wherein the first diffusion plate comprises at least one type of filter disposed as a grating of parallel strips.

8. The device of claim 6 wherein the first light is a first flash light.

9. The device of claim 5 wherein the second illuminating station comprises a second light having a second diffusion plate so that the second illuminating station emits a second diffuse light.

10. The device of claim 9 wherein the second diffusion plate comprises at least one type of filter disposed as a grating of parallel strips.

11. The device of claim 9 wherein the second light is a second flash light.

12. The device of claim 5 wherein the first diffuse light has a first direction of travel substantially perpendicular to a second direction of travel of the second diffuse light.

13. A device for detecting defects in a cylindrical glass housing comprising:

a first illuminating station positioned to illuminate the housing with a first diffuse light and create a first image;

a second illuminating station positioned to illuminate the housing with a second diffuse light and crate a second image;

a sensing station to sense the first image and the second image so as to detect defects and debris in the housing;

a first system to direct the first image to the sensing station;

a second system to direct the second image to the sensing station.

14. The device of claim 13 wherein the sensing station comprises a video camera having a polarization filter placed so that the first image and the second image are sensed only after the first image and the second image have passed through the polarization filter.

15. The device of claim 13 wherein the first illuminating station comprises a first light having a first diffusion plate so that the first illuminating station emits first diffuse light.

16. The device of claim 15 wherein the first diffusion plate comprises at least one type of filter disposed as a grating of parallel strips.

17. The device of claim 15 wherein the first light is a first flash light.

18. The device of claim 13 wherein the second illuminating station comprises a second light having a second diffusion plate so that the second illuminating station emits second diffuse light.

19. The device of claim 18 wherein the second diffusion plate comprises at least one type of filter disposed as a grating of parallel strips.

20. The device of claim 18 wherein the second light is a second flash light.

21. The device of claim 13 wherein the first diffuse light has a first direction of travel substantially perpendicular to a second direction of travel of the second diffuse light.

* * * * *

UNITED STATES PATENT AND TRADEMARK OFFICE
CERTIFICATE OF CORRECTION

PATENT NO. : 5,134,278
DATED : July 28, 1992
INVENTOR(S) : Lucien J. Nelen

It is certified that error appears in the above-indentified patent and that said Letters Patent is hereby corrected as shown below:

IN THE CLAIMS

Col. 6, line 48, before "cylindrical" delete "ad" and substitute therefor --and--; line 7, after the first occurrence of "area" delete "an" and substitute therefor --and--.

Col 7, line 20, after "image" delete "an" and substitute therefor --and--.

Col. 8, line 1, delete "4" and substitute therefor --6--.

Col. 8, line 25, delete "crate" and substitute therefor --create--.

Signed and Sealed this

Fourteenth Day of June, 1994

Attest:

BRUCE LEHMAN

Attesting Officer

Commissioner of Patents and Trademarks